United States Patent
Fischer et al.

(10) Patent No.: US 10,779,788 B2
(45) Date of Patent: Sep. 22, 2020

(54) REGISTRATION ON SETTING AN ALIGNMENT OF AN INSTRUMENT

(71) Applicant: Siemens Healthcare GmbH, Erlangen (DE)

(72) Inventors: Peter Fischer, Erlangen (DE); Thomas Fuchs, Buckenhof (DE); Philip Mewes, Nuremberg (DE); Holger Mönnich, Friedberg (DE); Martin Rube, Erlangen (DE)

(73) Assignee: Siemens Healthcare GmbH, Erlangen (DE)

( * ) Notice: Subject to any disclaimer, the term of this patent is extended or adjusted under 35 U.S.C. 154(b) by 0 days.

(21) Appl. No.: 16/225,855

(22) Filed: Dec. 19, 2018

(65) Prior Publication Data
US 2019/0192100 A1    Jun. 27, 2019

(30) Foreign Application Priority Data

Dec. 21, 2017    (DE) .................... 10 2017 223 598

(51) Int. Cl.
*G06K 9/00*    (2006.01)
*A61B 6/00*    (2006.01)
(Continued)

(52) U.S. Cl.
CPC ............ *A61B 6/5241* (2013.01); *A61B 6/032* (2013.01); *A61B 6/505* (2013.01); *A61B 34/10* (2016.02);
(Continued)

(58) Field of Classification Search
CPC ....... A61B 6/5241; A61B 34/10; A61B 90/36; A61B 6/032; A61B 6/505;
(Continued)

(56) References Cited

U.S. PATENT DOCUMENTS 6,304,050 B1 * 10/2001 Skaar .................... B25J 9/1692
                                                                  318/568.11
6,740,883 B1 *  5/2004 Stodilka ................ G01T 1/1648
                                                                  250/363.03
(Continued)

FOREIGN PATENT DOCUMENTS

CN        106974707 A     7/2017
DE     102013214479 A1    1/2015
(Continued)

OTHER PUBLICATIONS

Penney, Graeme P., et al. "A comparison of similarity measures for use in 2-D-3-D medical image registration." IEEE transactions on medical imaging 17.4 (1998): 586-595.*

(Continued)

*Primary Examiner* — Shefali D Goradia
(74) *Attorney, Agent, or Firm* — Lempia Summerfield Katz LLC

(57) ABSTRACT

A method is disclosed for registration on setting an alignment of an instrument relative to an object during a processing or treatment of the object by the instrument. A working image is registered to a planning image. The working image is recorded in a viewing direction that is selected dependent upon relevant degrees of freedom of the instrument such that the relevant degrees of freedom are the degrees of freedom with the greater registration accuracy. In addition, a robot system is provided which is configured for carrying out the method.

14 Claims, 2 Drawing Sheets

(51) Int. Cl.
*A61B 6/03* (2006.01)
*A61B 90/00* (2016.01)
*A61B 34/10* (2016.01)
*G06T 7/33* (2017.01)

(52) U.S. Cl.
CPC .............. *A61B 90/36* (2016.02); *G06T 7/33* (2017.01); *A61B 2034/107* (2016.02); *A61B 2090/367* (2016.02); *A61B 2090/376* (2016.02); *G06T 2200/04* (2013.01); *G06T 2207/10028* (2013.01); *G06T 2207/30004* (2013.01)

(58) Field of Classification Search
CPC ........ A61B 2034/107; A61B 2090/367; A61B 2090/376; G06T 7/33; G06T 2200/04; G06T 2207/10028; G06T 2207/30004
See application file for complete search history.

(56) References Cited

U.S. PATENT DOCUMENTS

| | | | | |
|---|---|---|---|---|
| 2004/0152970 | A1* | 8/2004 | Hunter | G06F 19/00 600/424 |
| 2008/0234575 | A1 | 9/2008 | Klingenbeck-regn | |
| 2011/0060341 | A1* | 3/2011 | Angibaud | A61B 17/155 606/89 |
| 2011/0158479 | A1 | 6/2011 | Homan | |
| 2015/0030229 | A1 | 1/2015 | Borsdorf | |
| 2016/0058399 | A1 | 3/2016 | Narabu | |
| 2018/0092699 | A1* | 4/2018 | Finley | A61B 17/7083 |

FOREIGN PATENT DOCUMENTS

| | | |
|---|---|---|
| JP | H09173350 A | 7/1997 |
| JP | 2005095281 A | 4/2005 |
| JP | 2008061858 A | 3/2008 |
| JP | 2011530318 A | 12/2011 |
| WO | WO2014181870 A1 | 11/2014 |

OTHER PUBLICATIONS

Miao, Shun, Rui Liao, and Marcus Pfister. "Toward smart utilization of two X-ray images for 2-D/3-D registration applied to abdominal aortic aneurysm interventions." Biomedical Engineering and Informatics (BMEI), 2011 4th International Conference on. vol. 1. IEEE, 2011.

Tomazevic, Dejan, et al. "3-D/2-D registration of CT and MR to X-ray images." IEEE transactions on medical imaging 22.11 (2003): 1407-1416.

Japanese Office Action for Japanese Application No. 2018-238294 dispatched Mar. 31, 2020, with English translation.

* cited by examiner

REGISTRATION ON SETTING AN ALIGNMENT OF AN INSTRUMENT

CROSS REFERENCE TO RELATED APPLICATIONS

This application claims the benefit of DE 10 2017 223 598.5 filed on Dec. 21, 2017, which is hereby incorporated by reference in its entirety.

FIELD

Embodiments relate to a method for registration on setting an alignment of an instrument, and a robot system.

BACKGROUND

The treatment or processing of an individually shaped object using an instrument often requires an equally individual alignment of the instrument relative to the object. The actual treatment or processing is therefore routinely preceded by a planning phase in which an individual procedure is planned. This is of particular importance in the treatment of patients in the clinical environment, where the object is a patient and the treatment or processing is an operation or other treatment. In the context of an imaging-assisted treatment, before a, for example surgical, intervention, a three-dimensional planning image of the patient or at least of the affected body region is generated. Then, on the basis of this planning image, the treatment to be carried out is planned. This often includes a plurality of operational steps, for example the placement of an instrument at a particular site or the guidance of an instrument along a particular trajectory.

In order to carry out the treatment or processing as planned, the planning image must be brought into coincidence with the actually existing situation during the treatment or processing, that is, the object must be brought into a defined relationship to the instrument. This typically takes place in the context of what is known as a registration, during which after the placement of the object and before the intervention, one or more images are generated that are then compared with the planning image and brought into coincidence therewith, e.g. are registered as a whole. Given additional knowledge of the relationship between the instrument and the additional images, the alignment of the instrument may then be corrected, so that the subsequent treatment or processing is also actually carried out in the originally planned manner—e.g. as intended on the basis of the planning image.

SUMMARY AND DESCRIPTION

The scope of the present disclosure is defined solely by the appended claims and is not affected to any degree by the statements within this summary. The present embodiments may obviate one or more of the drawbacks or limitations in the related art.

Embodiments provide an improved method for the registration that leads to the greatest possible precision with regard to the alignment of the instrument relative to the object, so that a treatment or processing of the object takes place as accurately as possible and as originally planned.

An embodiment provides for registration on setting an alignment of an instrument relative to an object during a treatment or processing of the object by the instrument. The method is therefore a registration method. The setting of the alignment of the instrument and the processing or treatment of the object do not belong to the registration method, but are parts of other methods. However, the execution of the registration method takes place in conjunction with and accompanying, such other methods. In place of the expression pair "treatment or processing", without restricting the generality, the expression "treatment" is used in the following.

The instrument is movable and includes a plurality of degrees of freedom of movement. During the treatment, at least one operational step is specified in which the alignment of the instrument relative to the object is specified. The operational step per se does not belong to the registration method. In the operational step, the setting of the alignment is required only with respect to a subset of the degrees of freedom implying that the setting of the alignment with respect to the subset of the degrees of freedom is required to have a greater accuracy than for the other degrees of freedom. In the context of the method, the degrees of freedom with respect to which a setting of the alignment is required are determined and stored as relevant degrees of freedom.

Initially, a three-dimensional planning image of the object is provided. The three-dimensional planning image may be a three-dimensional image, also referred to as a 3D planning image or simply as a planning image. The planning image may be generated outside the method in a separate planning method and may be provided for the method, although the planning image may be generated as part of the method. In respect of a medical treatment or processing, thus for example, in an operation, the planning image may also be called a preoperative image.

In the method, using an imaging system, at least a two-dimensional working image of the object is generated. The two-dimensional working image may be a two-dimensional image and may also be referred to as a 2D working image or simply as a working image. The working image may be generated during the treatment and accordingly, specifically not in a separate planning method. In respect of a medical treatment, that is for example, in an operation, the working image may also be called an intraoperative image. As a result, therefore, there are at least two images. The two images have a different dimensionality.

The two-dimensional working image includes an image plane and is recorded in a direction of view, e.g. with a perspective that is not parallel to the image plane and that lies, for example, perpendicularly to the image plane, that is, to the working image itself. Furthermore, the working image is recorded in a recording direction that in some cases is identical to the viewing direction, e.g. in the case of camera images or X-ray images, depending upon the imaging method, although it may deviate therefrom due to technical circumstances, e.g. in ultrasonic images or special X-ray images that are recorded as sectional images. In order to be able to record the working image in a particular viewing direction, the imaging system is set in a corresponding recording position or is moved into such a recording position.

In the context of the method, the working image is registered to the planning image. The two images are brought into coincidence. Due to the different dimensionality of the two images, by the registration, there results for some of the degrees of freedom, a greater registration accuracy than for the other degrees of freedom. The degrees of freedom are therefore assigned to one of two groups of degrees of freedom, where the degrees of freedom of a first group have a greater registration accuracy than the remaining degrees of freedom that belong to a second group.

The working image is recorded in a viewing direction and correspondingly is recorded from a recording position that is selected dependent upon the relevant degrees of freedom. The imaging system is thus moved into a corresponding recording position so that a working image is recorded from the desired viewing direction. The viewing direction and accordingly the recording position are selected such that the relevant degrees of freedom are the degrees of freedom with the greater registration accuracy. The working image is thus recorded with a special orientation such that for the relevant degrees of freedom, a good registration accuracy results. In other words: the working image includes an image plane and a corresponding orientation that are selected dependent upon the relevant degrees of freedom such that for the relevant degrees of freedom, the greatest possible registration accuracy results. Therefore, with the method, by a selection of the viewing direction and thus of the image plane, the registration accuracy with respect to the relevant degrees of freedom may be improved, e.g. maximized, for the working image in a specified operational step.

The actual setting of the alignment of the instrument itself and correspondingly also the operational step are not component parts of the method, as already indicated. Rather, the operational step and any further operational steps are part of the treatment, which represents a separate method. The registration method described serves only for the preparation of the actual setting of the alignment and the operational step by a registration. A central aspect of the method is then accordingly the registration of the planning image to the working image. The setting of the alignment following completed registration is therefore significant for the method to the extent that on the basis of the planned setting of the alignment, it is determined from which viewing direction the working image will be recorded. Any movement of the instrument and overall the actual treatment of processing of the object by the instrument are therefore not part of the method.

The treatment may be an operation, e.g. a medical intervention on or in a patient as the object of the treatment. In place of the expressions "treatment" and "processing", the general expression "manipulation" is also used. In the clinical or medical context, the greatest possible registration accuracy is particularly desirable. Alternatively, the object is a workpiece that is formed or reshaped in the context of the treatment or processing and is generally processed. The object is an actual body, e.g. a real object and not merely a virtual object.

The operational step is one of a plurality of operational steps that are carried out successively, which is one after another. Each operational step therefore corresponds to a treatment or processing step. In each operational step, the instrument is thus generally moved, e.g. for example brought into position, set, positioned, guided, driven, advanced or the like.

The instrument may be suitable for treating or processing and is, for example, a needle, a drill, a cutting tool, a probe or the like. In one variant, the instrument is a part or a component that is added to the object or is to be inserted thereinto. The part is, for example, a screw. The instrument is alternatively also designated a tool.

In the present scenario, a planning image of the object is either already present or is generated. The planning image is in any event not generated during the actual treatment, but prior thereto in a planning method, e.g. in a planning phase. During this planning phase no actual treatment of the object yet takes place, rather the planning phase serves for the determination of the starting situation and of the individual planning of the treatment in advance. An essential feature of the planning phase is that the object may still move thereafter or may change its position. The planning phase typically takes place immediately before the treatment and thus at the location thereof, although alternatively spatially separated from the later treatment. In the clinical context, the patient is suitably firstly positioned on an operating table and thereafter the planning image is generated. Subsequently, the patient is treated or processed on the same operating table. Errors due to possible movements of the patient following the recording of the planning image are prevented by the registration to the working image during the operation.

The planning image is a three-dimensional image of the object, so that a detailed planning of the treatment in a plurality of dimensions is possible. In a suitable embodiment, the planning image is an X-ray image and is generated, for example, in the context of a CT scan, e.g. by computed tomography. Also suitable by contrast are other, particularly optical, images, for example an image generated by an MRI scan or by PET scan.

The instrument includes a plurality of degrees of freedom of movement, or for short, degrees of freedom. Subsequently, and without restricting the generality thereof, it will be assumed that the instrument includes a total of six degrees of freedom, specifically three each of translational and rotational degrees of freedom. In other words: the instrument is displaceable in respectively the direction of an x-axis (e.g. in an x-direction), a y-axis (e.g. in a y-direction) and a z-axis (e.g. in a z-direction) and is rotatable about the x-axis, the y-axis and the z-axis. This applies, for example, in an instrument that is guided by a robot arm. Altogether, the instrument is transferable thereby by one or more translations or by one or more rotations or by a combination thereof from a first alignment into a second alignment. The expression "setting the alignment" is thus to be understood, for example, to imply that the instrument is transferred from a first alignment into a second alignment, by which the spatial position or the spatial orientation is changed, or both. To this extent, the instrument is thus also movable.

In a given operational step, the instrument is to be aligned in a particular manner relative to the object. The alignment of the instrument is thus planned in advance and is known and is thus a planned alignment of the instrument in the specific operational step. In a suitable embodiment, the alignment takes place with the aim of bringing the instrument to a particular location on the object, for example, a penetration site for a needle. Alternatively, or additionally, the alignment takes place with the aim of subsequently moving the instrument along a specific direction, for example, into the object. The alignment therefore takes place with the aim of positioning the instrument at a particular site of the object or of moving it along a particular trajectory. In the operational step thereafter, a particular alignment is specified for the instrument relative to the object. The alignment of the instrument is characterized in an imaginary coordinate system with x, y and z axes by, for example, of six coordinates that define the position along, respectively, the x, y and z axis and a respective rotation about the axes.

In order to be able to carry out the treatment as planned, the working image of the object is registered to the planning image thereof. In an embodiment, the working image is an X-ray image. Suitable, by contrast however, are also other types of optical images. The working image includes, as compared with the planning image, a reduced dimensionality and is therefore easier and quicker to generate than a three-dimensional image, for example, during the treatment. The working image, as a two-dimensional image, is a perspective projection of the per se three-dimensional object in an image plane. Due to the reduced dimensionality, however, the working image includes a correspondingly lower information content.

During registration, a transformation with, for example, six degrees of freedom is determined that links the planning image and the working image to one another. The registration of a 3D planning image to a 2D working image is called 2D-3D registration for short. The accuracy during the registration, also called the registration accuracy, includes a direct influence on the accuracy during the setting of the alignment of the instrument, e.g. on the instrument accuracy. This is also influenced, for example, by the accuracy of the positioning of a robot arm and of a robot system, e.g. by the positioning accuracy of a robot. The registration accuracy corresponds to the instrument accuracy.

The working image may be recorded by an imaging system. In an embodiment, the imaging system is linked to the instrument such that the position relative to one another is known. In an embodiment, the imaging system and the instrument are each part of a robot system. In a first variant, the imaging system and the instrument are mounted together on a robot arm of the robot system and in a variant, the imaging system and the instrument are mounted separately, each on one of two robot arms of the robot system.

A precondition in the setting of the alignment of the instrument on the basis of a registration of two images is that one of the images is linked in a known manner to the instrument. For example, the working image is linked to the instrument so that the relative spatial relationship between the working image and the instrument is known in advance. In other words: the working image is generated by an imaging system and the imaging system is registered to the instrument. By the registration of the planning image to the working image, the instrument is then also automatically registered to the planning image.

The working image further differs from the planning image, for example, in that the working image is generated in the concrete situation of the treatment, so that the relationship between the instrument and the object is also detected. The working image is thus generated during the treatment. The working image is generated before or during one of the operational steps, e.g. before or during the operational step, so that the operational step is prepared or monitored, or both, by a registration to the planning image. Since the working image is created during the treatment, the preparation or monitoring of the corresponding operational step takes place online, e.g. during or in the course of the treatment and thus particularly in line with demand and goal-oriented.

Embodiments are based on the problem that the information content in the working image is disadvantageously lessened due to the reduced dimensionality. For example, depth information cannot be acquired from a two-dimensional image or only to a limited extent. For example, although information may be acquired from the working image in the image plane, it cannot be acquired along the viewing direction. The registration to the planning image and therefore automatically also the positioning of the instrument, thus take place in the image plane with a high degree of accuracy, perpendicularly thereto, however, it is taken with severely restricted accuracy. Accordingly, for the different degrees of freedom of the instrument, different accuracy levels result. The registration accuracy with regard to a particular degree of freedom is therefore dependent on its relative position in relation to the viewing direction and the image plane of the working image. Translations along the image plane and rotations about an axis perpendicular to the image plane (e.g. the degrees of freedom within the image plane) may be registered with a higher degree of accuracy than a translation perpendicular to the image plane and rotations about axes parallel to the image plane (e.g. the degrees of freedom outside the image plane).

The aforementioned problem of the reduced information content may in principle be circumvented in that a plurality of working images are recorded from different viewing directions and are combined. The approach, however, is correspondingly costly, for example, time-consuming. For the recording of a plurality of working images from different viewing directions, the imaging device used, e.g. an X-ray device, must be aligned multiple times accordingly and also requires a correspondingly large operating range. The approach with a plurality of working images is therefore suitable only to a limited extent as an online method, e.g. for execution during the treatment or processing.

In the present case, it has also been recognized that in an operational step, not all the degrees of freedom of the instrument are necessarily of the same significance and that in a given operational step, the requirements for accuracy with respect to the individual degrees of freedom are different. Underlying this is the recognition, for example, that in the treatment, depending upon the intended alignment, e.g. positioning or guiding, of the instrument in a specific operational step, not all the degrees of freedom are of equal significance, but that depending upon the type of operational step, particular degrees of freedom are more relevant, e.g. more important than others. This is elucidated with the following example: on placement of a needle or alternatively a drill, the positioning on the surface of the object is initially of primary importance in order to be able to reach the intended site correctly during the subsequent insertion. During this subsequent insertion of the needle into the object, however, the penetration angle and forward movement of the needle, e.g. the penetration depth, is particularly important. If the needle points, for example, in the z-direction, then during positioning, it is primarily the x-direction and the y-direction that are significant. During insertion, it is then primarily the z-direction and the rotations about the x-axis and the y-axis that are significant.

It has further been recognized that the accuracy for the individual degrees of freedom of the instrument depends primarily on the alignment of the working image relative to the instrument. Making reference to the above example, an image that is recorded in the direction of the needle or the drill, that is in the z-direction, is particularly suitable for the lateral positioning of the needle, e.g. for alignment in the image plane, that is in the x-direction and the y-direction. By contrast therewith, an image that is recorded laterally, that is from the side of the needle, is particularly suitable for insertion of the needle since, from the side, the penetration angle and the penetration depth are particularly readily recognizable.

Embodiments provide a specially selected and as far as possible optimum viewing direction for the working image, the best possible registration, that is, the greatest possible registration accuracy, and thus also the greatest possible instrument accuracy. This is achieved in that during the selection of the viewing direction for the working image, it is considered which of the degrees of freedom of the instrument are particularly relevant. The working image is recorded such that the relevant degrees of freedom lie as far as possible in the image plane or at least such that the relevant degrees of freedom are as recognizable as possible in the working image.

The fact that the alignment for a given operational step is pre-known is now advantageously used in the registration for the purpose of later setting of this very alignment. For this purpose, it is firstly determined in relation to which degrees of freedom a setting is required, e.g. which degrees of freedom are relevant in the operational step, e.g. which degrees of freedom are important in the operational step and that are not. For a given operational step, the instrument is specifically not moved along all the degrees of freedom or positioned in relation to all the degrees of freedom, rather the movement or the positioning and thus in general the alignment is restricted to a subset of the degrees of freedom. The degrees of freedom that are used in a given operational step are also designated relevant degrees of freedom.

Another type of the 2D-3D registration is described, for example in the article "Toward smart utilization of two X-ray images for 2D-3D registration applied to abdominal aortic aneurysm interventions", Miao et al., Computers and Electrical Engineering 39 (2013), pp. 1485-1498. In the case disclosed there, depth information for a 2D image of the aorta is obtained from a 3D image of the spinal column in that the 3D image is used as a boundary condition for the spatial position of the aorta.

A further 2D-3D registration is described in the article "3D/2D Registration of CT and MR to X-Ray Images", Tomaževič et al., IEEE Transactions on Medical Imaging, Vol. 22 No. 11, November 2003, p. 1407 ff. As in the aforementioned article, anatomical circumstances are used here also as additional boundary conditions for improving the accuracy, in the present case, the orientation of bone surfaces.

In the aforementioned approaches, the information content of the images themselves is used to obtain the greatest possible registration accuracy. For this purpose, prior anatomical knowledge is used in the image processing and the determination of the derived boundary conditions. This is not significant in the present case. Rather, in the present case, an entirely different approach is pursued in which the registration accuracy is improved in that even the image generation, specifically the generation of the working image, takes place with regard to the operational step to be performed and taking account of the planned alignment of the instrument. Thus, rather than achieving the greatest possible accuracy only in the context of the image processing, it is ensured as early as before the generation of the working image that the working image leads in the subsequent processing to the greatest possible accuracy. In a suitable variant, however, both approaches are profitably combined with one another.

Since the operational step is already known, before the corresponding operational step and after the relevant degrees of freedom have been determined, the imaging system is suitably moved automatically into the respective optimum recording position and then the working image is recorded from the relevant viewing direction. The treatment is thereby significantly accelerated.

For a respective operational step, only the working images required for this are determined. The registration takes place in a workflow-oriented manner and for a particular degree of freedom only when a registration is also needed for it due to the operational step.

Since the registration takes place with the specific selection of the viewing direction precisely with regard to the relevant degrees of freedom, it is also only a single working image that is needed for a given operational step in order despite the reduced dimensionality to achieve an optimum accuracy for the corresponding operational step. The recording of further working images for the same operational step is especially not necessary. In an embodiment, therefore, for a respective operational step, only one working image is recorded.

With a plurality of operational steps, a treatment or processing-adapted image generation is possible and may also takes place. The treatment includes, for example, a plurality of successive operational steps. In an embodiment, after each operational step and immediately before the subsequent operational step in the context of the registration method, a re-registration is carried out in that for the subsequent operational step, a further working image is recorded that is registered to the planning image. The further working image is recorded as described above dependent upon the relevant degrees of freedom of the subsequent operational step in order for further working image to maximize the registration accuracy as far as possible. In other words, the degrees of freedom with respect to which a setting of the alignment is required for the subsequent operational step are determined anew and stored as new relevant degrees of freedom. The further working image is thus recorded in a new viewing direction that is selected dependent upon the new relevant degrees of freedom such that the new relevant degrees of freedom are the degrees of freedom with the greater registration accuracy. The new viewing direction for the working image of the subsequent operational step is however possibly not necessarily another viewing direction from that of the operational step for the preceding operational step. If the viewing direction is identical for two successive operational steps, for the later operational step, one working image is dispensed with and instead the working image of the previous operational step is used anew.

For each of a plurality of operational steps, therefore a working image adapted to the respective operational step is then generated and is registered to the planning image. It is taken into account that different degrees of freedom are also relevant in the different operational steps and that then for each operational step, an optimum and operational step-adapted registration is carried out with a maximum registration accuracy for the relevant degrees of freedom. Possible existing calibration errors have significantly less or no effect, since for each operational step, the registration takes place in that calibration errors are present entirely or mainly in the non-relevant degrees of freedom, whereas the relevant degrees of freedom have a significantly improved accuracy. The operational step-adapted registration is designated a re-registration or as workflow-adapted imaging. The generation of the working images is thus carried out operational step-related, e.g. the viewing direction is determined for a particular operational step and may deviate from the optimum viewing direction for another operational step. What is important is that the working image serves for registration for a particular operational step and that the viewing direction is selected with a view to the operational step such that for the degrees of freedom of the instrument relevant in this operational step, the greatest possible registration accuracy results.

An initial coarse registration is carried out in that the planning image is generated while the object is at the location of the later treatment, e.g. in a treatment position. The position of the object then changes at most slightly from the planning phase to the treatment. In the coarse registration, the planning image matches the actual position. The coarse registration is thus not a registration in the proper sense since two different images are not placed spatially in relation to one another. The initial coarse registration then serves more broadly as a starting point for the next registrations by a working image.

However, alternatively or additionally to the coarse registration described above, in an embodiment, the planning image is recorded before a treatment and not at the location of the later treatment. Subsequently, a coarse registration is then suitably carried out in that two working images are recorded from two different directions.

The planning image is generated by the same imaging system as the later working image. All the working images and the planning image are recorded by the same imaging system if in the context of the treatment, a plurality of working images is generated. In an embodiment, the treatment of the object is carried out immediately following the planning phase. Possible movements of the object after completion of the planning phase are thereby prevented as far as possible. In addition, a coarse registration as described above is provided with little effort in terms of equipment. An X-ray device (e.g., a computed tomography system or CT system) that may generate both 3D and 2D images may be used.

In an embodiment, the imaging system is an X-ray device. The X-ray device includes a C-arm that includes an X-ray radiation source and a detector. The working image is generated in that the C-arm is advanced toward the object in a suitable position. The detector is configured, for example, as a detector field that provides the recording of a two-dimensional image with an image plane that is parallel to the detector and perpendicular to a radiation direction from the X-ray radiation source to the detector.

The instrument and the imaging system are, for example, also registered to one another, since for the most accurate possible execution of the treatment or processing, the spatial relationship between the instrument and the imaging system is also significant. By the most accurate possible registration of the instrument to the imaging system, relative errors between the instrument and the object may be reduced. In an embodiment, the instrument and the imaging system are already registered to one another at the start of the method and also at the start of the treatment or processing. In an embodiment, the instrument and the imaging system are registered to one another alternatively or additionally during the treatment or processing in that during the creation of the working image, the instrument is also imaged in the working image and in that subsequently, on the basis of the working image, the position of the instrument relative to the imaging system is determined. The already recorded working image is thus used in addition to the registration of the object with the instrument to register the instrument to the imaging system. The overall accuracy is further improved.

The method is suitable for registration with a plurality of highly varied operational steps.

In an embodiment, in the operational step, a position of the instrument on the object, for example on a surface of the object, is specified and the setting of the position takes place purely by a translation along two translation directions. The two translation directions are determined and stored in the context of the method as relevant degrees of freedom. The viewing direction is selected to be perpendicular to the translation directions and, for example, along the instrument. The planned operational step serves for the positioning of the instrument relative to the object and within a working plane that is determined by the two translation directions. The two translation directions are, for example, the x-axis and the y-axis, along which the instrument is movable and is also moved to approach the position in the operational step. The other four degrees of freedom of the instrument are not relevant in this case. An optimum registration accuracy is produced in that the imaging system records the working image from such a recording position in which the viewing direction is perpendicular to the working plane. "Perpendicular" does not imply exclusively "exactly perpendicular", but rather a viewing direction deviating slightly therefrom is still possible, however, with an increasing deviation, the accuracy becomes lessened. For example, a viewing direction that lies at an angle of at least 85° to the working plane may be suitable.

In an embodiment, in the operational step, a penetration angle of the instrument relative to the object is specified and the setting of the penetration angle takes place purely through rotation of the instrument about a rotation axis. The rotation axis is determined and stored as a relevant degree of freedom. The viewing direction is then selected to be along the rotation axis. A rotation of the instrument in the drawing plane is then executable with a high level of accuracy. For the registration it is not necessarily required with regard to a greatest possible accuracy in the setting of the penetration angle that the viewing direction is selected to be exactly along the rotation axis. Rather, in this regard also, correspondingly slightly deviating viewing directions are still suitable for achieving a high level of registration accuracy. A viewing direction that lies at an angle of not more than 5° relative to the rotation axis may be suitable.

The planned operational step thus serves for the rotation or the inclination of the instrument relative to the object. In a preceding positioning within a working plane as described above, but also in general, a penetration angle of the instrument into the object may be set or altered. If the instrument has already penetrated into the object, a penetration angle or advancing direction of the instrument may be changed or corrected.

Insofar as the instrument lies in the field of view of the imaging system and is then visible in the working image, the instrument is shown therein, for example, in a lateral view, e.g. the instrument then lies in the image plane. The viewing direction thus points laterally to the instrument.

In a further embodiment, in the operational step, a penetration depth of the instrument into the object is specified and the setting of the penetration depth takes place purely through a translation of the instrument along an advancing direction. The advancing direction is determined and stored as a relevant degree of freedom. The viewing direction is selected to be perpendicular to the advancing direction. In this embodiment, the registration takes place with the aim, in the subsequent operational step of being able to move the instrument into the object accurately up to a specified penetration depth. The instrument is thus to be moved along a trajectory up to a specific target point. The viewing direction and the image plane are therefore selected such that the trajectory lies specifically within the image plane. Here also, the principle applies that slightly deviating viewing directions are also still suitable, for example, those that lie at an angle of at least 85° to the advancing direction.

Suitably, during the execution of the operational step, the setting of the alignment of the tool is monitored by the imaging system, for example, recurrently. The monitoring, but not the movement of the instrument, is carried out as part of the registration method. This is based upon the concept that the imaging system is already set by the preceding registration in an optimum recording position for a monitoring of the movement of the instrument in the subsequent operational step. Any deviations from the planned alignment may be observed with particularly great accuracy. For this purpose, during the operational step, an image is accordingly recorded that corresponds in principle to the working image, but also shows the progressive movement of the instrument. An online monitoring of the operational step is then carried out.

Embodiments may be used in the clinical setting and for the improvement of an imaging-supported treatment of a patient, who is the object of the treatment. In an application, the treatment is a spinal column operation that includes at least three operational steps. The general descriptions set out above also apply accordingly for the specific application during a spinal column operation. The instrument is a needle, for example, for the administration of an anesthetic agent, a drill, for example, for creating a bore hole in a vertebra of the patient, or a screw that is to be placed into the vertebra, e.g. into a previously created bore hole. The instrument may extend along a longitudinal axis.

During the spinal column operation, the instrument is to be advanced into the object from outside to a specified penetration site, specifically at a specified penetration angle, so that a particular site of the spinal column is reached. This applies for all three of the described variants of the instrument. The procedure is carried out for each of the named instruments, so that firstly an anesthesia is carried out with a needle and subsequently a preparation of a vertebra with a drill and finally the insertion of a screw into the vertebra. With respect to a single instrument, a first operational step is then a placement of the instrument on the patient, a second operational step is a setting of a penetration angle of the instrument and a third operational step is a penetration of the instrument into the patient. The operational steps are carried out successively in the stated sequence. The three operational steps are then carried out anew for each of the instruments.

In the context of a spinal column operation with the stated operational steps, the viewing direction is selected to be along the longitudinal axis. For the second and the third operational step, the viewing direction is selected to be perpendicular to the longitudinal axis of the instrument. During the third operational step, the penetration of the instrument is suitably monitored repeatedly by the imaging system. By this specific selection of the viewing directions in the individual operational steps, an optimal registration accuracy is achieved for each of the operational steps and the operation is carried out with significantly improved accuracy. The operational steps per se correspond to those that are usually carried out in the context of an imaging-supported spinal column operation. To this extent, the method is usable without difficulty in normal spinal column operations, with no or only slight changes to the operating procedure of a treating clinician result.

The method may be used, for example, in the context of a robot-supported treatment or processing in which the instrument and the imaging system are each components of a robot system. The robot system is configured for treating or processing an object and includes an instrument for treating or processing the object, and an imaging system for recording at least one working image and suitably also for recording a planning image. The robot system further includes a control unit that is configured to carry out the registration method described above. The control unit may also be referred to as a controller. The control unit is, for example, a part of a control system for controlling the individual parts of the robot system. The robot system serves altogether, firstly for carrying out the treatment or processing and, secondly, is configured so that during treatment or processing, the registration method is carried out in order to improve the accuracy of the treatment or processing accordingly.

DETAILED DESCRIPTION

Figure 1:
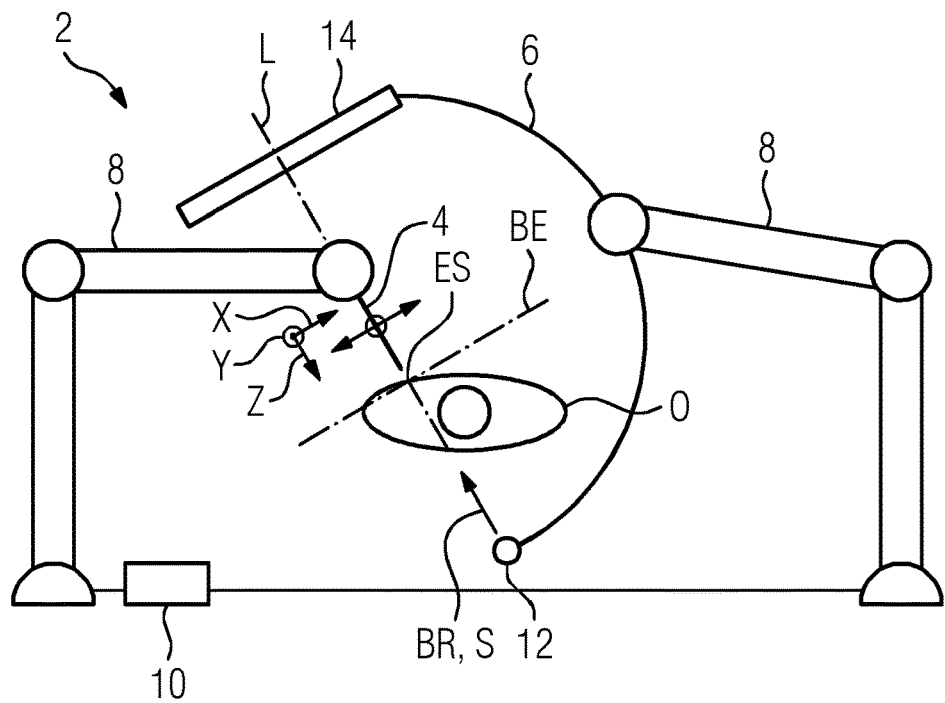
FIG. 1 depicts an example registration for a first operational step
Figure 2:
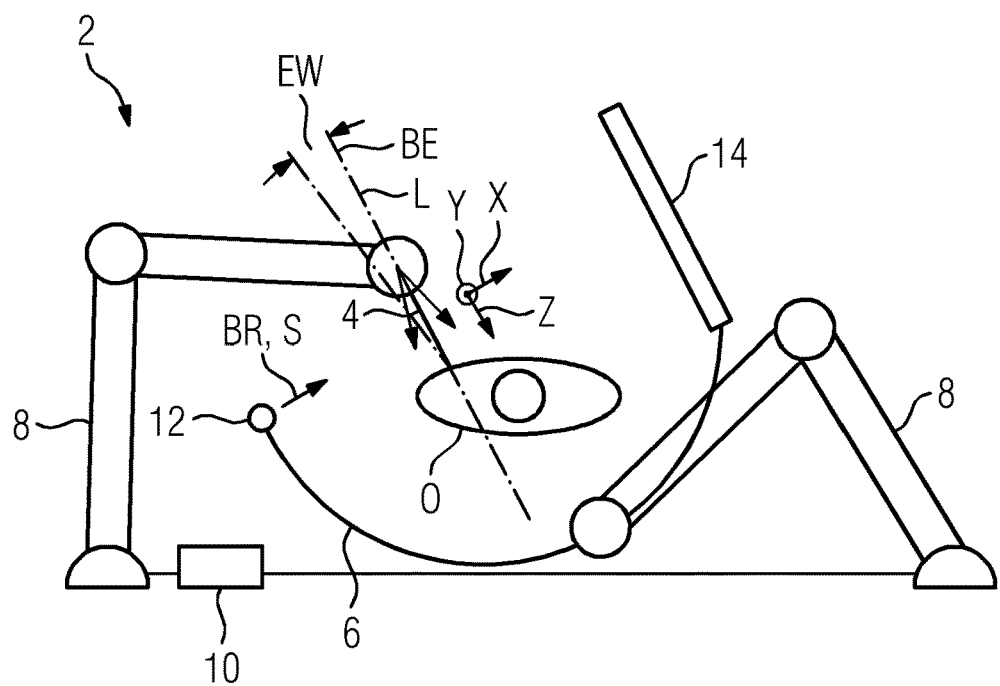
FIG. 2 depicts an example registration for a second operational step.
Figure 3:
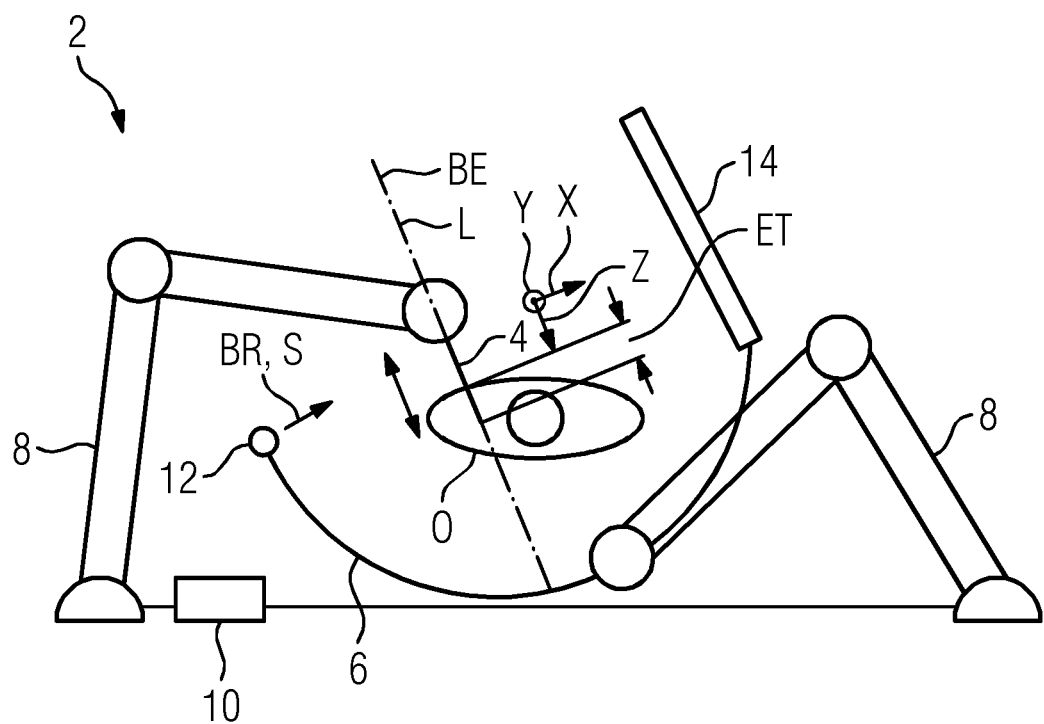
FIG. 3 depicts an example registration for a third operational step.

In FIGS. 1 to 3 a treatment or processing of an object O is shown, in this example a spinal column operation, where the object O is a patient. The patient is shown in the drawings from above in a lying position. Indicated schematically are the torso and head of the patient.

The treatment is carried out under robot-assistance with a robot system 2. The robot system includes an instrument 4 for treating the object O. The instrument 4 is, for example, a needle, a drill, cutting tool, a probe or the like or is a part or a component, e.g. a screw, that is added to the object O or is to be inserted thereinto. The robot system 2 further includes an imaging system 6 for recording at least one working image and in the present case also for recording a planning image. All the working images and the planning image are consequently recorded by the same imaging system 6. In the embodiment shown, the imaging system 6 and the instrument 4 are separately mounted each on one of two robot arms 8 of the robot system 2. The robot system 2 further includes a control unit 10 that is configured to carry out a specific registration method accompanying the treatment.

The instrument 4 is movable and includes a plurality of, in the present case six, degrees of freedom of movement, specifically three each of translational and rotational degrees of freedom. In other words, the instrument 4 is displaceable in the direction of an x-axis X, a y-axis Y and a z-axis Z and is rotatable about each of the axes X, Y, Z. In a defined operational step, the instrument 4 is to be aligned in a specified manner relative to the object O, wherein the alignment takes place with the aim of positioning the instrument 4 at a particular site of the object O or of moving it along a particular trajectory. The alignment of the instrument 4 is therefore characterized in an imaginary coordinate system with the axes X, Y, Z by six coordinates that define the position along, respectively, the axes X, Y, Z and a respective rotation about the axes.

In the present case, the imaging system 6 is an X-ray device and includes a C-arm that includes an X-ray radiation source 12 and a detector 14. The working image is then generated in that the C-arm is advanced in a suitable position toward the object O. The detector 14 is configured as a detector field that provides the recording of a two-dimensional image with an image plane BE that is parallel to the detector 14 and perpendicular to a radiation direction S from the X-ray radiation source 12 to the detector 14. The imaging system 6 is connected to the instrument 4 such that their relative position to one another is known, since for the most accurate possible execution of the treatment, the spatial relationship between the instrument 4 and the imaging system 6 is also significant. For this purpose, the instrument 4 and the imaging system 6 are registered to one another.

In preparation for the treatment, a preoperative, three-dimensional planning image of the object O is generated in a manner not described in detail and is then provided for the method. Additionally, an initial coarse registration is carried out in which the planning image is generated while the object O is at the location of the later treatment, e.g. on an operating table (not shown in detail). In the coarse registration, the planning image matches the actual position of the object O.

During the treatment, by the imaging system 6, in order to prepare a respective operational step, an operational step-specific, two-dimensional intraoperative working image of the object O is generated. The working image includes an image plane BE and is recorded in a viewing direction BR that lies perpendicularly to the image plane BE and in the present case, corresponds to the radiation apparatus S.

The method serves for registration during the treatment for the purpose of the improved setting of an alignment of the instrument 4 relative to the object O. For this purpose, the working image is now registered and thereby linked in the context of a 2D-3D registration to the planning image. The accuracy during the registration, also designated the registration accuracy, has a direct influence on the accuracy during the setting of the alignment of the instrument 4, e.g. on the instrument accuracy.

During the treatment, for each operational step, a particular alignment of the instrument 4 relative to the object O is now specified. Therein, in a particular operational step, not all the degrees of freedom of the instrument 4 are necessarily of the same significance, so that in a given operational step, the requirements for accuracy with respect to the individual degrees of freedom are different.

Depicted in FIGS. 1 to 3 are three different situations in each of which a special registration is carried out in order to achieve the greatest possible accuracy in the subsequent operational step. In the present case, for each operational step, just one working image is recorded from a viewing direction BR that is selected dependent upon the degrees of freedom that are relevant for the respective operational step. FIGS. 1 to 3 depict the imaging system 6, in each case in an optimum recording position with respect to the corresponding operational step.

During the spinal column operation shown by way of example, the instrument 4 is to be moved into the object O from outside to a specified penetration site ES, specifically at a specified penetration angle EW, so that a particular site of the spinal column is reached. A first operational step is then an approach to the penetration site ES, a second operational step is a setting of the penetration angle EW and a third operational step is a penetration of the instrument 4 up to a specified penetration depth ET. The operational steps are carried out successively in the stated order.

For the first operational step, the viewing direction BR is selected to be along the longitudinal axis L of the instrument 4 as shown in FIG. 1, that is, in the direction of the z-axis Z. In general, for the first operational step, a position of the instrument 4 on a surface of the object O is specified. The setting of the position takes place by a translation along two translation directions, specifically in FIG. 1 along the x-axis X and the y-axis Y, that together define a working plane that lies perpendicularly to the drawing plane of the figures. The x-axis X and the z-axis Z lie in the drawing plane and the y-axis Y is perpendicular thereto. The translations in the x-direction and in the y-direction are thus the relevant degrees of freedom in the present case. The other four degrees of freedom of the instrument are not relevant in this case. The imaging system 6 records the working image from the recording position shown in FIG. 1 in which the viewing direction BR is perpendicular to the working plane.

For the second and third operational step, the viewing direction BR is selected, as depicted in FIGS. 2 and 3, respectively perpendicular to the longitudinal axis L of the instrument 4 and in the direction of the x-axis X and thus perpendicular to the recording position in FIG. 1.

In the second operational step, the penetration angle EW that is set purely by rotating the instrument 4 about a rotation axis X, Y, Z is specified, specifically in the present case about the x-axis X, that is out of the drawing plane of the figures, as indicated in FIG. 2 by the double-headed arrow. The x-axis X is therefore the relevant degree of freedom in the present case in relation to the second operational step. The viewing direction BR is selected as shown in FIG. 2 along the x-axis X. In the working image, then, the instrument 4 is to be seen in a lateral view.

In the third operational step, the penetration depth ET is specified and the instrument 4 is simply moved along an advancing direction, in the present case along the z-axis Z as depicted in FIG. 3. The z-axis Z is then determined in relation to the third operational step as a relevant degree of freedom and is stored. The viewing direction BR is selected, as is recognizable in FIG. 3, perpendicular to the z-axis and in the present case in the direction of the x-axis X, that is, identically to the viewing direction as in FIG. 2, so that in a variant for the third operational step, no working image is recorded, rather the working image for the second operational step is simply used again.

During the third operational step, the penetration depth ET of the instrument 4 is additionally monitored repeatedly by the imaging system 6. In this regard therefore, an online monitoring is then carried out. The recording position of FIG. 3 is maintained.

Overall, consequently, in the context of the method, the degrees of freedom with respect to which a setting of the alignment is required are determined and stored as relevant degrees of freedom. The working image for a respective operational step is recorded in a viewing direction BR that is selected such that the relevant degrees of freedom are the degrees of freedom with the higher registration accuracy. Use is also made thereby of the fact that the accuracy for the individual degrees of freedom of the instrument 4 depend primarily on the alignment of the working image relative to the instrument 4. Making reference to FIG. 1, a working image that is recorded in the direction of the z-axis Z is well suited to the lateral positioning of the instrument. By contrast therewith, a working image that is recorded from the side of the instrument 4 as shown in FIGS. 2 and 3 is suitable for the insertion since, from the side, the penetration angle EW and the penetration depth ET are readily recognizable. The working image is recorded such that the relevant degrees of freedom lie as far as possible in the image plane BE.

It is to be understood that the elements and features recited in the appended claims may be combined in different ways to produce new claims that likewise fall within the scope of the present disclosure. Thus, whereas the dependent claims appended below depend from only a single independent or dependent claim, it is to be understood that these dependent claims may, alternatively, be made to depend in the alternative from any preceding or following claim, whether independent or dependent, and that such new combinations are to be understood as forming a part of the present specification.

While the present disclosure has been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description.

The invention claimed is:

1. A method for registration on setting an alignment of an instrument relative to an object during a processing or treatment of the object by the instrument, wherein the instrument is movable and includes a plurality of degrees of freedom of movement, the method comprising:
specifying, during the treatment or processing, at least one operational step, in which the alignment of the instrument relative to the object is defined and in which the setting of the alignment is required only in relation to a subset of degrees of freedom of the plurality of degrees of freedom;
determining and storing, as relevant degrees of freedom, the subset of degrees of freedom;
providing a three-dimensional planning image of the object;
generating, by an imaging system, a two-dimensional working image of the object in a viewing direction that is selected dependent upon the relevant degrees of freedom; and
registering the two-dimensional working image to the planning image so that a higher degree of registration accuracy results for some degrees of freedom of the plurality of degrees of freedom than for other degrees of freedom of the plurality of degrees of freedom.

2. The method of claim 1, wherein for a respective operational step, only one two-dimensional working image is generated.

3. The method of claim 1, wherein the treatment or processing comprises a plurality of consecutive operational steps, and
wherein after an operational step and before the subsequent operational step in each case, a re-registration is carried out in that for the subsequent operational step, a further two-dimensional working image that is registered to the three-dimensional planning image is recorded.

4. The method of claim 1, further comprising carrying out an initial coarse registration, the carrying out of the initial coarse registration comprising generating the three-dimensional planning image while the object is at the location of the treatment.

5. The method of claim 1, wherein the three-dimensional planning image is generated by the same imaging system as the two-dimensional working image.

6. The method of claim 1, wherein the imaging system is an X-ray device.

7. The method of claim 1, further comprising registering the instrument and the imaging system to one another during the treatment or processing, the registering of the instrument and the imaging system comprising:
imaging the instrument during the creation of the working image; and
subsequently, determining the position of the instrument relative to the imaging system based on the working image.

8. The method of claim 1, further comprising:
specifying, in the at least one operational step, a position of the instrument on the object; and
setting the position of the instrument purely by a translation along two translation directions; and
determining the two translation directions and storing the two translation directions as a degree of freedom of the relevant degrees of freedom,
wherein the viewing direction is selected to be perpendicular to the translation directions.

9. The method of claim 1, further comprising:
specifying, in the at least one operational step, a penetration angle of the instrument relative to the object; and
setting the penetration angle purely through rotation of the instrument about a rotation axis;
determining the rotation axis and storing the rotation axis as a degree of freedom of the relevant degrees of freedom,
wherein the viewing direction is selected to be along the rotation axis.

10. The method of claim 1, further comprising:
specifying, in the at least one operational step, a penetration depth of the instrument into the object;
setting the penetration depth purely through a translation of the instrument along an advancing direction;
determining the advancing direction and storing the advancing direction as a degree of freedom of the relevant degrees of freedom,
wherein the viewing direction is selected to be perpendicular to the advancing direction.

11. The method of claim 1, further comprising monitoring, during the execution of the at least one operational step, the setting of the alignment of the instrument by the imaging system.

12. The method of claim 1, wherein the object is a patient,
wherein the treatment or processing is a spinal column operation that comprises three operational steps,
wherein the instrument is a needle, a drill, or a screw and extends along a longitudinal axis,
wherein a first operational step of the three operational steps is a placement of the instrument on the patient,
wherein a second operational step of the three operational steps is a setting of a penetration angle of the instrument,
wherein a third operational step of the three operational steps is a penetration of the instrument into the patient,
wherein for the first operational step, the viewing direction is selected to be along the longitudinal axis,
wherein for the second operational step and the third operational step, the viewing direction is selected to be perpendicular to the longitudinal axis in each case, and
wherein during the third operational step, the penetration of the instrument is monitored repeatedly by the imaging system.

13. A robot system that is configured for treatment or processing of an object, the robot system comprising:
an instrument for the treatment or processing of the object;
an imaging system; and
a controller configured for registration on setting an alignment of the instrument relative to the object during the processing or treatment of the object by the instrument, wherein the instrument is movable and includes a plurality of degrees of freedom of movement, the registration comprising:
specification, during the treatment or processing, of at least one operational step, in which the alignment of the instrument relative to the object is defined and in which the setting of the alignment is required only in relation to a subset of degrees of freedom of the plurality of degrees of freedom;

determination and store, as relevant degrees of freedom, the subset of degrees of freedom;

provision of a three-dimensional planning image of the object;

generation, by the imaging system, a two-dimensional working image of the object in a viewing direction that is selected dependent upon the relevant degrees of freedom; and registration of the two-dimensional working image to the planning image so that a higher degree of registration accuracy results for some degrees of freedom of the plurality of degrees of freedom than for other degrees of freedom of the plurality of degrees of freedom.

14. The robot system of claim 13, wherein the imaging system is an X-ray device.

* * * * *